United States Patent [19]

Meyer

[11] 4,059,702

[45] Nov. 22, 1976

[54] 3,8-BIS-BASIC ETHERS OF 6H-DIBENZO[b,d]PYRAN-6-ONE

[75] Inventor: Donald R. Meyer, Goshen, Ohio

[73] Assignee: Richardson-Merrell Inc., Wilton, Conn.

[21] Appl. No.: 740,806

[22] Filed: Nov. 11, 1976

Related U.S. Application Data

[62] Division of Ser. No. 317,237, Dec. 21, 1972, abandoned.

[51] Int. Cl.$^2$ .............. C07D 413/14; C07D 311/80; A61K 31/365
[52] U.S. Cl. .............. 424/248.55; 544/79; 260/288 CF; 260/293.58; 260/293.62; 260/326.25; 260/326.5 C; 260/343.2; 260/570.7; 424/267; 424/274; 424/279
[58] Field of Search .............. 260/343.2 R, 326.25, 260/293.58, 246 B; 424/279, 267, 274, 248.55

[56] References Cited

U.S. PATENT DOCUMENTS 3,859,312  1/1975  Meyer et al. .............. 260/343.2 R

OTHER PUBLICATIONS

Umemoto et al., Chem. Abst. 1972, vol. 76, 73716s.
Kameda et al., Chem. Abst. 1974, vol. 80, 145956c.

*Primary Examiner*—Natalie Trousof
*Assistant Examiner*—Jane T. Fan
*Attorney, Agent, or Firm*—William J. Stein; Eugene O. Retter; George W. Rauchfuss, Jr.

[57] ABSTRACT

Bis-basic ethers of 9-sustituted phenanthrene and related 10-oxa and 10-aza derivatives, their method of preparation and their use as pharmaceutical agents for the prevention and inhibition of viral infections are disclosed.

7 Claims, No Drawings

3,8-BIS-BASIC ETHERS OF 6H-DIBENZO[b,d]PYRAN-6-ONE

This is a division of application Ser. No. 317,237, filed Dec. 21, 1972, now abandoned.

FIELD OF THE INVENTION

This invention relates to new organic chemical compounds, to their preparation and to pharmaceutical compositions containing such compounds. The compounds described herein are useful antiviral agents which inhibit or inactivate viruses by their administration to either an infected or to a non-infected host.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease and various immunological diseases and degenerative diseases of the central nervous system have been linked to viruses as the causative agents.

The present, the control of virus infections is primarily achieved by means of immunization vaccines. For example, poliomyelitis, smallpox, measles and influenza are well recognized diseases in which viral vaccines have proven effective. In general, however, viral vaccines have had only a moderate success in animal prophylaxis. Each vaccine acts primarily against a specific virus and is not heterophilic in the protection it offers. Hence, vaccines do not provide a practical solution against the wide array of infectious viruses, even where limited, as for example, solely to respiratory viruses.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further damage to cells and tissues of the animal host which have not as yet been infected. Heretofore, only a limited number of virus infections such as smallpox, Asian influenza and herpes keratitis have been susceptible to prevention by chemical antiviral agents. Sulfonamides and antibiotics which have revolutionized the treatment of bacterial infections have substantially no effect upon virus infections. Certain infections caused by large viruses, such as lymphogranuloma venereum, psittacosis and trachoma have been successfully treated using antibiotics and sulfa drugs. However, the majority of infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of antiviral agents which are bis-basic ether derivatives of 9-substituted phenanthrene and which also include their corresponding 10-oxa and 10-aza derivatives. A more descriptive designation for these compounds in accordance with Chemical Abstracts nomenclature would be to describe them as bis-basic ether derivatives of 9-phenanthrol, 6(5H)-phenanthridinone and 6H-dibenzo[b,d]pyran-6-one. These compounds are effective against a wide spectrum of viral infections and are useful in treating such infections either prophylactically or therapeutically.

U.S. Pat. No. 3,592,819 is the closest art known to applicants and discloses certain bis-basic ethers and thioethers of various substituted fluorenes, 9-fluorenols and 9-fluorenones useful as antiviral agents. Certain of the bis-basic ethers described therein serve as starting materials for the preparation of some of the compounds of the present invention.

The bis-basic ethers described and claimed herein, however, are derived from a totally different and chemically unrelated 6,6,6 tricyclic aromatic ring system which differs substantially from the fluorene nucleus. To applicants' knowledge the compounds described and claimed herein are novel compounds which have not been previously described nor reported in the literature. Additionally, applicants are unware of any previously reported bis-basic derivatives of 9-phenanthrol, 6(5H)-phenanthridinone or 6H-dibenzo[b,d]pyran-6-one which possess antiviral activity. The compounds described herein possess a wide spectrum of antiviral activity in varying degrees which could not have predicted from a knowledge of the present state of the art.

SUMMARY OF THE INVENTION

This invention relates to new derivatives of 9-substituted phenanthrene and to their related 10-oxa and 10-aza congeners, to their methods of preparation, compositions thereof, and to their usefulness as pharmaceutical agents. More particularly, the compounds of the present invention are 2,7-bis-basic ethers of 9-phenanthrol or 9-lower alkoxyphenanthrene, 3,8-bis-basic ethers of 6(5H)-phenanthridinone and 3,8-bis-basic ethers of 6H-dibenzo[b,d]pyran-6-one which are useful in the prevention or inhibition of viral infections. Still more particularly, the compounds of the present invention may be represented by the following general formulas:

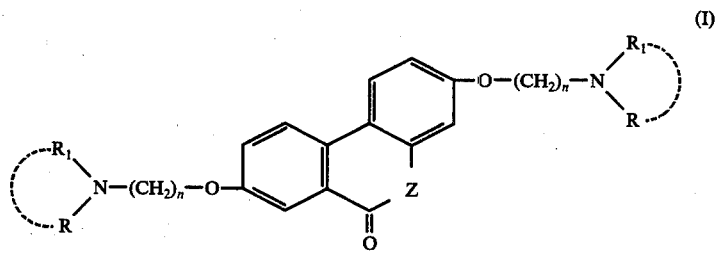

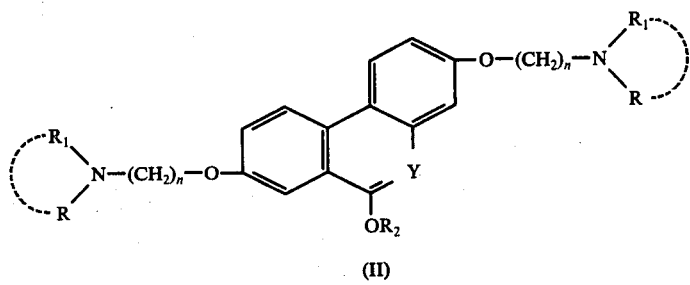

(II)

wherein n is an integer of from 2 to 6; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group, and when R and $R_1$ are taken together with the nitrogen atom to which they are attached represent the pyrrolidinyl, piperidino or morpholino radical; Z is selected from the group consisting of oxygen, imino and methylene; Y is nitrogen or methylidene; and $R_2$ is selected from the group consisting of hydrogen or lower alkyl having from 1 to 4 carbon atoms. The expression methylene is intended to refer to the —$CH_2$— radical, whereas the expression methylidene is intended to refer to the —CH+ radical.

The compounds represented in formulas (I) and (II) above include both the free base form as well as the pharmaceutically acceptable acid addition salts thereof. In general, the salts of these compounds are crystalline materials which are soluble in water and various hydrophilic organic solvents, and which, in comparison to their free base forms, generally exhibit higher melting points and an increased stability. Among the compounds represented by formula I are those in which Z is oxygen.

It should be noted that the bis-basic ether side chains appear in the same relative configuration for the 9-substituted phenanthrene, 6(5H)-phenanthridinone and the 6H-dibenzo[b,d]pyran-6-one series of compounds. However, due to the difference in numbering systems as shown below, the compounds of the present invention are designated as 2,7-bis-basic ethers for the phenanthrene series of compounds, whereas they are designated as 3,8-bis-basic ethers in both the phenanthridine and 6H-dibenzo[b,d]pyran series of compounds.

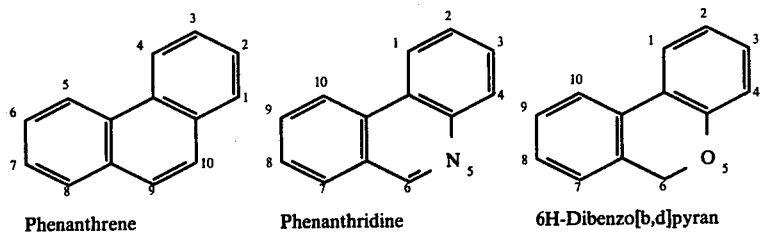

Phenanthrene     Phenanthridine     6H-Dibenzo[b,d]pyran

The 2,7-bis-basic ethers of 9-methoxyphenanthrene (V) are prepared via a ring enlargement of the related 2,7-bis basic ethers of fluoren-9-one (lll), which are found described in U.S. Pat. 3,592,819. This series of reactions can best be illustrated by means of the following reaction scheme in which the symbols n, R, $R_1$ and $R_2$ have the values previously assigned.

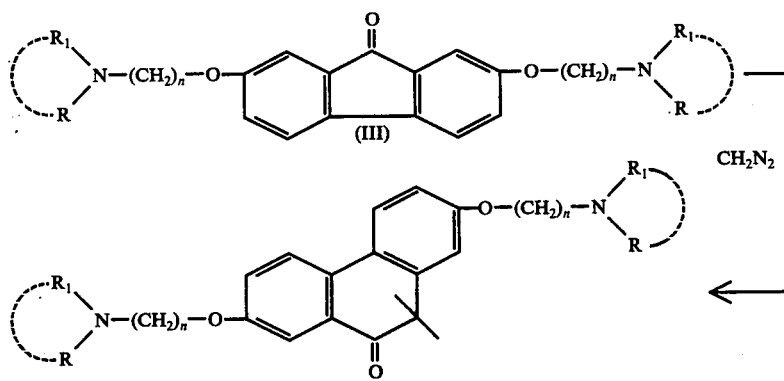

-continued

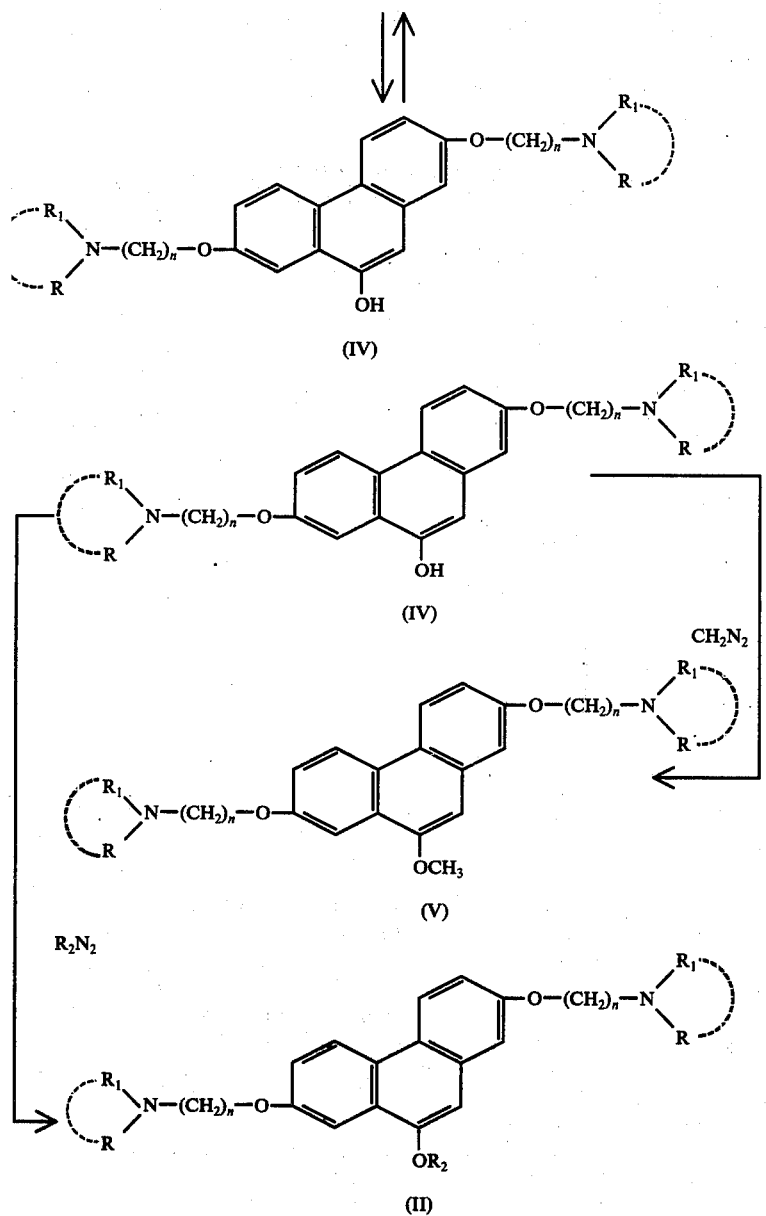

The 3,8-bis-basic ethers of 6(5H)-phenanthridinone (VI) are prepared via a hydrazoic acid ring expansion using the 2,7-bis-basic ethers of fluoren-9-one (III) in the presence of a strong mineral acid. This reaction can be illustrated by the following general reaction scheme in which the symbols $n$, R and $R_1$ have the same values previously assigned:

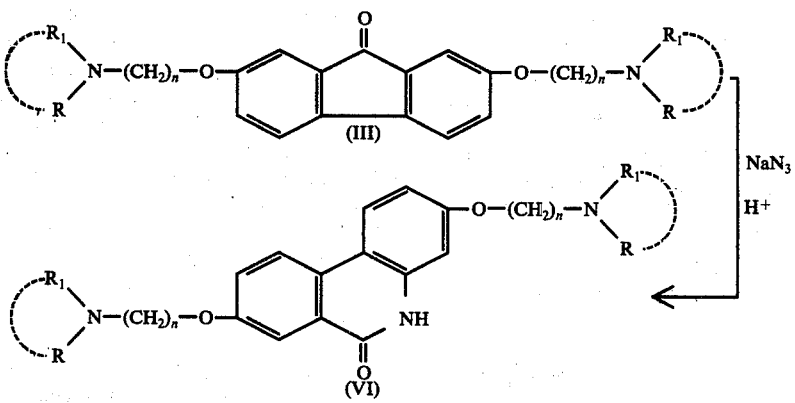

The 3,8-bis-basic ethers of 6H-dibenzo[b,d]pyran-6-one (X) can be prepared by means of a peracid or peroxide ring expansion of the related 2,7-bis($\omega$-haloalkyl)ethers of fluoren-9-one (VII) in the presence of a strong mineral acid. The 3,8-bis(ω-haloalkyl)ethers of 6H-dibenzo[b,d]pyran-6-one (VIII) so prepared are subsequently condensed with an amine (IX) to form the desired 3,8-bis-basic ethers of 6H-dibenzo[b,d]pyran-6-one (X). This reaction sequence can be illustrated by the following general reaction scheme in which the symbols $n$, R and $R_1$ have the values previously designated and the symbol Hal is chlorine, bromine or iodine.

The basic amino function represented by the symbol

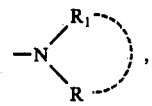

can be a primary, secondary or a tertiary amino group. Preferably, each amino group is a tertiary amine. The

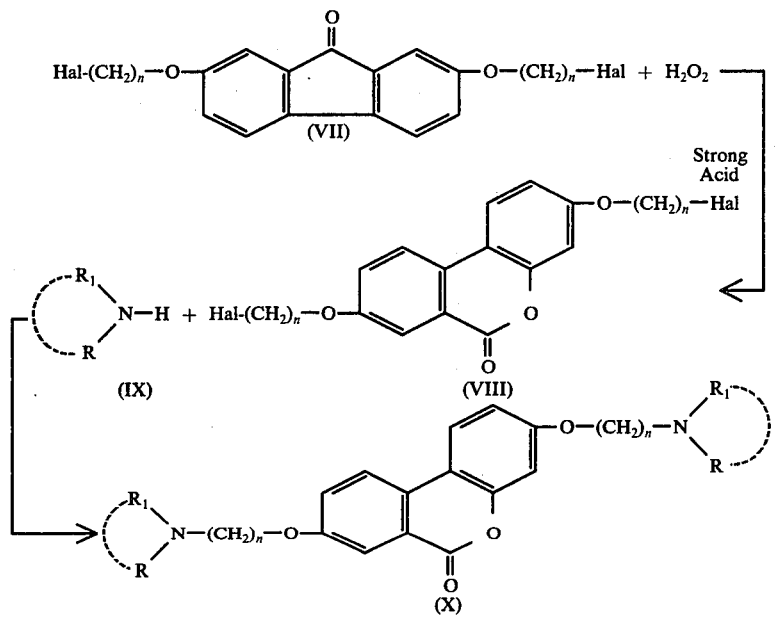

To achieve an antiviral effect the compounds of this invention are administered to a suitable host using a variety of compositions. Such compositions may be administered either prior to infection, as a prophylactic use or treatment, or they may be administered subsequent to infection of the host as a curative use or treatment.

A wide variety of compositions are also included within the scope of the present invention. Thus, the instant compounds may be applied externally or topically directly at the situs of infection, or they may be administered internally or systemically, irrespective of whether the treatment is prophylactic or curative in nature. In either event, replication of the infectious virus is inhibited or prevented with the concomitant result that the various disease symptoms characteristic of the pathogenic viral infection are either diminished or no longer present.

DETAILED DESCRIPTION OF THE INVENTION

As can be seen from general formulas (I) and (II) above, the compounds of the present invention encompass bis-basic ethers in which each side chain is linked to a benzenoid portion of the tricyclic nucleus. More specifically, these side chains are linked at the 2 and 7-positions in the phenanthrene series and at the corresponding 3 and 8 positions in the phenanthridine and 6H-dibenzo[b,d]pyran series. It can be further seen that the side chains consist essentially of a basic amino function at the terminal end of the chain, an ether bridging group at the proximal end of the chain with the basic amino function separated from the ether group by an alkylene chain of prescribed length.

symbols R and $R_1$ represent either hydrogen or a lower alkyl group. The term lower alkyl as used herein with regard to the basic amino function relates to groups having from 1 to 6 carbon atoms. Illustrative of such groups can be mentioned both straight or branched chain alkyl radicals such as: methyl, ethyl, $n$-propyl, isopropyl, $n$-butyl, sec-butyl, isoamyl, $n$-pentyl and $n$-hexyl. When R and $R_1$ each represent lower alkyl, a preferred subgenus is formed.

Each R and $R_1$ can also represent a cycloalkyl group having from 3 to 6 carbon atoms. Illustrative of such groups are the cyclopropyl, cyclobutyl, cyclopentyl and cyclohexyl radicals.

The symbols R and $R_1$ also represent an alkenyl group having from 3 to 6 carbon atoms. In addition to the unsaturation which must be present, this unsaturation must be in a position other than the 1-position of the alkenyl group in order to prevent hydrolysis from occurring. Illustrative of such groups are the allyl, 3-butenyl and the 4-hexenyl radicals.

R and $R_1$ may also be joined with the nitrogen atom to which they are attached to represent various saturated monocyclic, heterocyclic radicals. Typical of such heterocyclic groups are the 1-pyrrolidinyl, piperidino or morpholino radicals. Compounds containing these groups are readily prepared and typify saturated monocyclic, heterocyclic radicals which are generally useful in lieu of the dilower alkylamino groups present in the compounds of this invention.

The alkylene chain separating the basic amino function from the tricyclic ring consists of from 2 to 6 carbon atoms and can be either a straight or branched alkylene chain. The alkylene chain must separate the adjacent oxygen atom from the terminal amino nitrogen by at least 2 carbon atoms, i.e., the ether oxygen and amino nitrogen cannot share the same carbon atom of the alkylene group. Each of the alkylene groups can be the same or different, preferably, however, both alkylene groups are the same. Illustrative of such groups are ethylene, propylene, 1,3-propylene, butylene, 1,4-butylene, 2-methyl-1,4-butylene, pentamethylene, 3-methyl-1,5-pentylene and hexamethylene.

Illustrative of the base compounds of the present invention represented by generic formula (I) can be mentioned. 3,8-bis(4-piperidinobutoxy)-6(5H)-phenanthridinone, 2,7-bis[2-(diethylamino)ethoxyl]-9-phenanthrol, 3,8-bis[3-(N-cyclohexyl-N-methylamino)propoxy]-6H-dibenzo[b,d]pyran-6-one, 3,8-bis[2-(diisopropylamino)ethoxyl]-6-(5H)-phenanthridinone, 3,8-bis[2-(diisopentylamino)ethoxyl]-6H-dibenzo [b,d]pyran-6-one and 2,7-bis[2-( diallylamino)ethoxyl-9-phenanthrol.

It must also be recognized that compounds of formula (I) in which a hydrogen atom is available adjacent to the keto function are capable of forming the corresponding enol tautomers. Thus, in both phenanthrene and the 6H-phenanthridone series, the compounds of the present invention may also be represented by the general formula (IA) which is tautomeric with the corresponding keto form as illustrated below.

the base compounds of the present invention represented by general formula (II) there can be mentioned: 2,7-bis[2-(diethylamino) ethoxyl]-9-methoxyphenanthrene, 2,7-bis[3-(1-pyrrolidinyl) propoxyl]-9-propoxyhenanthrene, 2,7-bis[2-(cyclohexylamino) ethoxy]-9-methoxyphenanthrene, 2,7-bis[4-(diallylamino) butoxyl]-9-methoxyphenanthrene, 3,8-bis[2-(diethylamino) ethoxy]-6-methoxyphenanthridine and 3,8-bis[4 -(dimethylamino)butoxyl]-6-ethoxyphenanthridine.

The expression "pharmaceutically acceptable acid addition salts" is intended to apply to any non-toxic organic or inorganic acid addition salts of the base compounds represented by formulas (I) and (II). Illustrative inorganic acids which form suitable salts include hydrochloric, hydrobromic, sulfuric and phosphoric acids as well as acid metal salts such as sodium monohydrogen orthophosphate and potassium hydrogen sulfate. Illustrative organic acids which form suitable salts include the mono, di and tricarboxylic acids. Illustrative of such acids are, for example, acetic, propionic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic and sulfonic acids such as methanesulfonic acid and 2-hydroxyethanesulfonic acid. Either the mono or the di-acid salts can be formed,

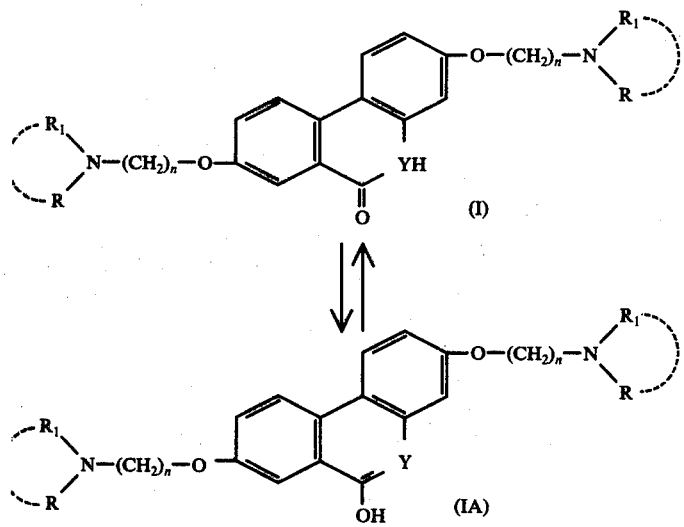

In the above representation, it is understood that the symbol Y is limited to nitrogen and the CH group only. Where the oxygen atom is present, as in the 6H-dibenzo[b,d]pyran series of compounds, there is, of course, no enolizable hydrogen available and the compounds exist only in their keto form. It is further understood that the compounds in the phenanthrene and phenanthridine series are likely to be mixtures of tautomeric forms, the compositions of which are dependent upon such factors as the nature of the tricyclic nucleus, the various side chains present and the environment surrounding the molecule as a whole. In the case of the phenanthrene series, the enol or phenolic form predominates.

The enol form can be stabilized by a replacement of the enol hydrogen in this position with a lower alkyl group as represented by the symbol $R_2$. Thus, the 6 and/or 9-lower alkyl ethers exist only in compounds of the phenanthrene and phenanthridine series respectively, whereas the 6H-dibenzo[b,d]pyran series of compounds exist only as 6-keto compounds and do not form the corresponding 6 -lower alkyl ethers. Illustrative of and such salts can exist in either a hydrated or a substantially anhydrous form.

In general the compounds of the present invention are prepared from various 2,7-disubstituted-9-fluorenous precursors which are more fully described in U.S. Pat. No. 3,592,819. The preparation of the instant compounds involves various ring expansions of the 9-fluorenone nucleus to form the corresponding 9-substituted phenanthrene, 6(5H)-phenanthridinone and 6H-dibenzo[b,d]pyran-6-one rings. More particularly, the reaction with diazomethane results in the formation of the 2,7-bis basic ethers of 9-methoxyphenanthrene; the reaction with hydrazoic acid results in the formation of 3,8-bis basic ethers of 6(5H)-phenanthridinone; whereas the reaction with peracids or hydrogen peroxide results in the formation of the 3,8-bis basic ethers of 6H-dibenzo[b,d]pyran-6-one.

Cyclic aliphatic ketones are known to ring expand with diazomethane to form larger cyclic aliphatic ketones. This reaction may be also be conducted in some instances with aromatic ketones, producing a variety of homologous ring-enlarged ketones in addition to the formation of enols, enol ethers and ethylene oxides. Thus, for example, Schultz et al, J. Am. Chem. Soc. 62, 2902-4 (1940) reported the reaction of diazomethane with fluorenone to yield 5% of 9-phenanthrol, 30% of 9-methoxyphenanthrene, 1.5% of di-9-phenanthryl ether, an unknown substance and 30% of unchanged fluorenone. In addition, substituents on the aromatic ring are known to change the ratio of the various products obtained as well as to give rise to additional isomeric, homologous ketones and side products. Thus, the application of the diazomethane reaction to the 2,7-bis-basic ethers of 9-fluorenone could not have been predicted and is not without difficulty.

The reaction is most frequently conducted by treatment of a methanolic solution of the carbonyl containing compound with an ethereal solution of diazomethane, either in the presence or absence of a catalyst. Alternatively, a solution of the carbonyl compound in methanol is treated with nitrosomethylurethane in the presence of a base. The diazomethane can be prepared either ex situ or in situ. Generally, applicants prefer to generate the diazomethane ex situ and to co-distill the diazomethane so produced with ether into a methanolic solution of the carbonyl containing compound. Suitable inert solvents which may also be utilized include such solvents as dioxane, benzene, toluene, chloroform and methylene chloride with ether-methanol being the solvent combination of choice. Additionally, methanol has been shown to have a high catalytic activity for diazomethane ring expansion reactions. Catalysts which may be usefully employed in this reaction include trace amounts of metal salts such as zinc chloride or lithium chloride. A minimum of 2 equivalents of diazomethane are generally employed, one equivalent providing for the ring expansion, whereas the other equivalent competes with the starting material to form the corresponding 9-methoxyphenanthrene ethers (V). In addition to a variety of side products which are formed, some of the intermediate 2,7-bis basic ethers of 9-phenanthrol (IV) also remain. The intermediates are readily separated from the reaction mixture in the form of their sodium salts. The 9-lower alkoxyphenanthrene derivatives (II), other than the 9-methoxyphenanthrene derivatives, are prepared, in turn, by the reaction of the 9-phenanthrols (IV) with other lower diazoalkanes.

Due to the complex and wide variety of side reactions possible, no more than 8 equivalents of diazomethane are useful in the preparation of the 2,7-bis-basic ethers of 9-methoxyphenanthrene. The reaction proceeds exothermally and is conducted at room temperature or below. The reaction takes place at a temperature range of from about −50° C. to ambient temperatures with a temperature of 0° C. conveniently preferred. The reaction can be conducted for a period ranging anywhere from about one hour to about seven days.

The 9-phenanthrol derivatives, which are also formed in the diazomethane ring expansion reaction, are readily freed of their nonacidic materials by extraction with chloroform from a strongly alkaline reaction mixture. The 9-phenanthrol derivatives which remain in the aqueous medium may then be removed by neutralization of the aqueous medium to a pH of about 9-10, and subsequently extracting the neutralized medium with chloroform. The 9-phenanthrols so obtained can then be etherified by reacting with a lower diazoalkane to form the corresponding 9-lower alkoxy phenanthrene ethers.

The preparation of the 3,8-bis-basic ethers of 6(5H)-phenanthridinone (VI) is achieved via a modification of the so-called Schmidt reaction. Essentially, as applied here, this method inserts a hetero nitrogen atom via a ring expansion into the five membered fluoren-9-one ring using hydrazoic acid in the presence of a strong mineral acid such as sulfuric acid to form the six-membered heterocyclic ring of 6(5H)-phenanthridone. Hydrazoic acid is known to react with simple cyclic ketones to form ring enlarged cyclic amides or lactams. Thus, for example, cyclohexanone reacts with hydrazoic acid yielding caprolactam. Approximately equimolecular quantities of hydrazoic acid are used inasmuch as an excess of hydrazoic acid encourages tetrazole formation. The reaction can be conducted by the addition of a solution of hydrazoic acid in an appropriate organic solvent to a solution of the fluoren-9-one. Alternatively, hydrazoic acid can be generated in situ by the addition of sodium azide to the reaction mixture. Due to the extremely hazardous nature of hydrazoic acid, the use of sodium azide is preferred, thereby eliminating the necessity for the isolation of the toxic hydrazoic acid. This reaction is exothermic in nature, and consequently the reaction is best conducted by stirring with a suitable means for cooling. The reaction can be conducted at temperature ranges of from about −20° C. to about 50° C., and for periods of from about 30 minutes to about 1 week. Generally, a temperature of 0° C. with a reaction period of about 1 hour is preferred as a matter of convenience. If the reaction appears to proceed sluggishly, higher temperatures can be advantageously employed. Due to the rapidity of the reaction with hydrazoic acid, the reaction is conveniently controlled by the rate of addition of the hydrazoic acid or sodium azide to a stirred solution of the 9-fluorenone derivative dissolved or suspended in a suitable solvent. Suitable solvents include sulfuric acid, chloroform, benzene, dioxane and diethyl ether with trifluoroacetic acid having been found to be particularly useful. Generally, sodium azide is added in small increments to a trifluoroacetic acid solution of the 9-fluorenone ether derivative, until no further evolution of nitrogen gas is observed. At this point the reaction is considered to be complete for all practical purposes. An acid catalyst is also employed. Any strong acid may be used with concentrated sulfuric acid being the catalyst of choice. Isolation of the 3,8-bis basic ethers of 6(5H)-phenanthridinone so prepared is achieved using standard procedures apparent to those skilled in the art. An alternative route to the preparation of the 6(5H)-phenanthridinone ethers is via a Beckmann rearrangement of the corresponding fluorenone oximes. Moore and Huntress, J. Am. Chem. Sc. 49, 2618 (1927), have demonstrated the preparation of 7-nitro-6(5H)-phenanthridinone by the treatment of 2-nitrofluoren-9-one oxime with phosphorous pentachloride dissolved in phosphorous oxychloride. In similar fashion the 3,8-bis basic ethers of 6(5H)-phenanthridinone can be prepared from the 2,7-bis-basic ethers of fluoren-9-one oxime as illustrated in the following reaction scheme:

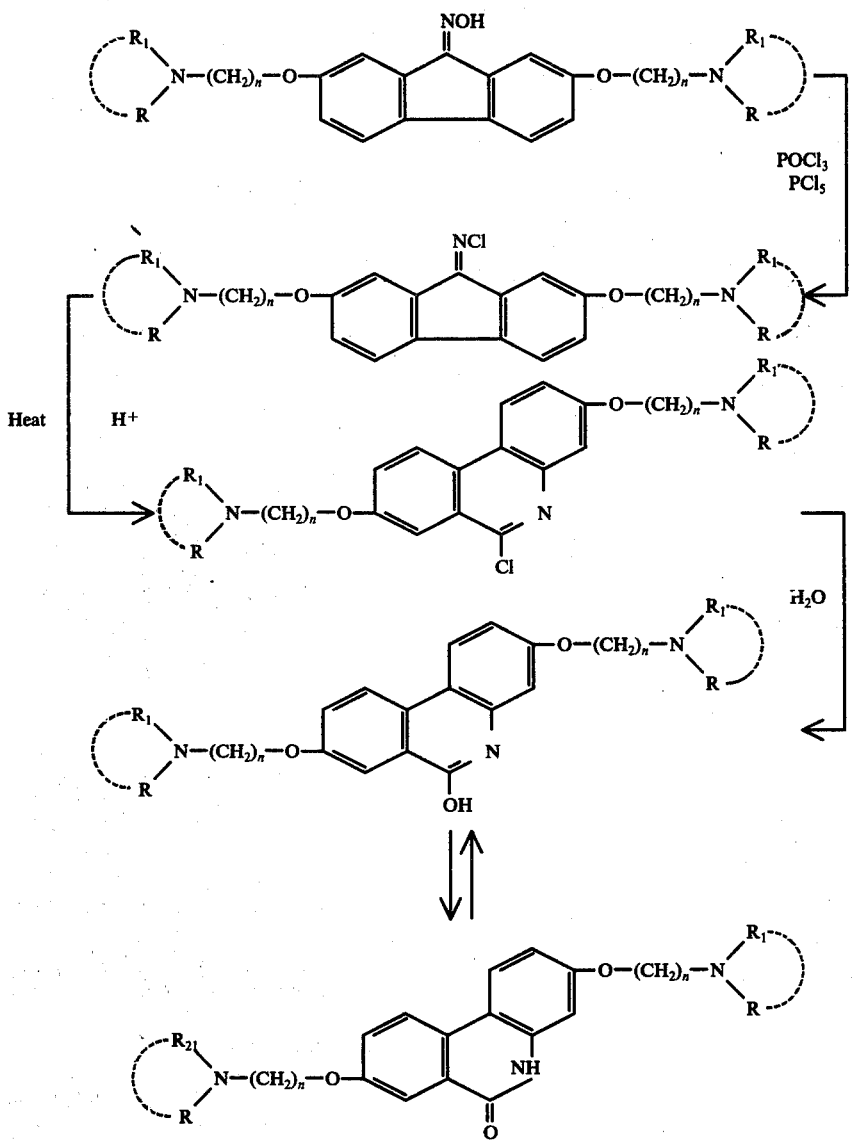

The first step in the preparation of the 3,8-bis-basic ethers of 6H-dibenzo[b,d]pyran-6-one involves the peracid or peroxide oxidation of a 2,7-bis(ω-haloalkyl) ether of fluoren-9-one (VII) under Baeyer-Villiger conditions. Essentially, this reaction results in a ring expansion of the five-membered fluoren-9-one ring with the introduction of an oxygen atom to form a six-membered ring expanded lactone or 6H-dibenzo[b,d]pyran-6-one nucleus. Thus, the oxidation of a 2,7-bis (ω-haloalkyl) ether of fluoren-9-one (VII), found described in U.S. Pat. No. 3,592,819, with a peracid or hydrogen peroxide in the presence of a strong acid, such as sulfuric acid, results in the formation of a 3,8-bis (ω-haloalkyl) ether of 6H-dibenzo[b,d]pyran-6-one (VIII). The 6H-dibenzo[b,d]pyran (ω-haloalkyl) ethers so prepared can then be condensed with an amine (IX9 to form the desired 3,8-bis-basic ethers of 6h-dibenzo[b,d]pyran-6-one (X), the compounds of the present invention. The oxidation reaction is exothermic in nature and the temperature of the reaction mixture may be conveniently controlled by the rate of addition of the oxidizing agent. The reaction temperatures vary from about −20° to 40° C., with a temperature of about 25° C. being preferred. Reaction times range anywhere from about 30 minutes to about one week at the lower temperatures. Large excesses of peroxide are to be avoided inasmuch as there is always the hazard of peroxide oxidations occurring with explosive violence. If significant amounts of peroxide remain upon completion of the reaction, they can be decomposed using reducing agents such as sodium bisulfite or ferrous sulfate. Generally, a two or three fold excess of hydrogen peroxide is satisfactory in carrying out the ring expansion. The reaction is favored by polar solvents and proceeds in a variety of solvents such as sulfuric acid, acetic acid or acetic anhydride. The 3,8-bis(ω-haloalkyl) ethers of 6H-dibenzo[b,d]pyran-6-one (VIII) so prepared are subsequently condensed for the second step in the preparation of the 3,8-bis basic ethers of 6H-dibenzo[b,d]pyran-6-one (X).

The condensation reaction of the bis(ω-haloalkyl) ethers (VIII) with an amine (IX) can be carried out using a variety of conditions. For example, the ethers can be heated together with a large excess of amine, the excess amine serving both as the reaction medium and the hydrohalide acceptor. This method is particularly suitable for those amines which are readily available, inasmuch as any excess amine can be readily removed from the reaction mixture via distillation at a reduced pressure or by steam distillation. Alternatively, the ω-haloalkyl ethers (VIII) can be heated with an excess of the amine in a suitable organic solvent. Suitable organic solvents include benzene, toluene, xylene and chlorobenzene, lower molecular weight alcohols such as methanol, ethanol and isopropyl alcohol, or they may include lower molecular weight ketones such as acetone and methyl ethyl ketone. The reaction of these ethers with an amine is generally promoted by the addition of either sodium or potassium iodide, the iodide being used in either catalytic or stoichiometric amounts. In some cases, as when the amine is expensive or in short supply, it may be advantageous to use only two equivalents of the amine for each equivalent of the ω-haloalkyl ether employed in the presence of an excess of either powdered sodium or potassium carbonate as the acceptor for the hydrohalide that is generated. In the case of volatile amines the condensation reaction can best be conducted under pressure in a suitable bomb or autoclave.

The compounds of the present invention are antiviral agents. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Illustratively such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative a mammalian virus infections which can be prevented or inhibited by the administration of the compounds of the present invention are infections caused by picornaviruses, such as encephalomyocarditis virus; myxoviruses, such as influenza $A_2$ (Jap/305) virus; arboviruses; such as Semliki forest virus; the herpes group of viruses, including herpes simplex; and the poxviruses, as for example vaccinia I HD. Thus, for example, the compounds of the present invention when administered orally or subcutaneously to mice in varying doses either shortly prior to subsequent to a fatal inoculation of a neurotropic virus such as encephalomyocarditis virus, having a $LD_{50}$ anywhere from 5 to 50, delay to prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used for each treated group with an additional 20 mice serving as a control group. At the time of administration the test virus is titrated in order to determine the potency of $LD_{50}$ for the particular virus pool used as a challenge. The control animals are given a placebo containing the identical volume of vehicle without, of course, the active ingredient. Because of the lethal nature of the test system employed, the antiviral nature of the test compound is dramatically illustrated by a side by side comparison of the survival time of treated animals with the untreated control group of animals.

Respiratory viruses, such as influenza $A_2$ (Jap/305) virus, which are also lethal to the test animals employed, are administered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-induced infection in the mouse, or perhaps due to some genetic factor or other natural defense mechanism not presently understood. For this reason the control group selected is of sufficient size as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus generally produces a nonfatal infection in mice, producing characteristic tail lesions when the virus is subcutaneously administered to the tail of the mouse. The instant compounds are administered either orally or subcutaneously either prior to or subsequent to the vaccinia infection. Tail lesions are subjectively scored on the eighth day following infection against untreated animals which serve as a control group. The compounds of the present invention have been found to be effective in varying degrees against one or all of these test virus systems.

The mode of activity of the active ingredients of the present invention is not rigourously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce a virus inhibiting substance, which inhibits in some yet unknown manner the intracellular replication of the virus without appearing to have any inactivation effect per se upon the virus itself. A few of the viruses susceptible to interferon replication inhibition are described in Horsfall and Tamm, "Viral and Rickettsial Infections of Man" 4th Edition (1965), J. B. Lippincott Company, pp. 328-329.

As previously indicated, the compounds of the present invention may be prophylactically administered in order to prevent the spread of contagious viral diseases or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively dosage levels of the administered active ingredients for intravenous treatment range from about 0.1 mg to about 10 mg per kg of body weight; for intraperitoneal administration range from about 0.1 mg to about 50 mg per kg of body weight; for subcutaneous administration range from about 0.1 mg to about 250 mg per kg of body weight; for oral administration may be from about 0.1 mg to about 500 mg per kg of body weight; for intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, e.g., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosate unit may contain from about 2.0 mg to cover 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5% to about 25% by weight, and preferably from about 1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A suitable method of administration for the compounds of the present invention is orally either in a solid dose form such as a tablet or capsule, or in a liquid dose form such as an elixir, suspension, emulsion or syrup. Ordinarily the active ingredient comprises from about 0.5% to about 10% by weight of an oral liquid composition. In such compositions, the pharmaceutical carrier is generally aqueous in nature, as for example, aromatic water, a sugar-based syrup or a pharmaceutical mucilage. For insoluble compounds suspending agents may be added as well as agents to control viscosity, as for example, magnesium aluminum silicate or carboxymethylcellulose. Buffers, preservatives, emulsifying agents and other excipients can also be added.

For parenteral administration such as intramuscular intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above identified HLB, or a mixture of two or more components having the desired HLB. Illustrative of surfactants useful in parenteral formulations are the class of polyoxyethylene sorbitan fatty acid ethers as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising liquid pharmaceutical excipients previously mentioned.

The active ingredients of the present invention can also be admixed directly with animal feeds or incorporated into the drinking water of animals. For most purposes, an amount of active ingredient is used which provides from about 0.0001% to about 0.1% and preferably from about 0.001% to about 0.02% by weight of the active ingredient based upon the total weight of feed intake. The active ingredients can be admixed in animal feed concentrates, suitable for use by farmers or livestock groweers for incorporation in appropriate amounts with the final animal feeds. These concentrates ordinarily comprise from about 0.5% to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred bacause of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples:

EXAMPLE I 2,7-Bis[2-(diethylamino)ethoxy]fluoren-9-one dihydrochloride

A solution of [2-(diethylamino)ethyl]chloride obtained from 15.5 g (0.09 mole) of [2-(diethylamino)ethyl]chloride hydrochloride in 100 ml of toluene (dried over molecular sieves) is added to a mixture of 6.4 g (0.03 mole) of 2,7-dihydroxy-fluoren-9-one and 3.3 g (0.06 mole) of sodium methoxide in 200 ml of toluene (dried over molecular sieves). The resulting mixture is heated to its reflux temperature with stirring for a period of 3 hours. Upon cooling, the mixture is filtered to remove the precipitated sodium chloride. The toluene solution is washed 3 times with water, once with saturated sodium chloride solution and dried over anhydrous magnesium sulfate. This mixture is filtered and the filtrate acidified to Congo Red with ethereal hydrogen chloride. The solid which precipitates in filtered, recrystallized from butanone with sufficient methanol being added to effect solution, and the product dried at 100° C. for 24 hours under vacuum: m.p. 235°–7° C., $\lambda_{max}^{H2O}$ 269, and $E_{1cm}^{1\%}$ 1600.

EXAMPLE II

2,7-BIS
2-(diethylamino)ethoxy]-9-methoxyphenanthrene

A solution of 11.7 g (0.028 mole) of 2,7-bis[2-(diethylamino)ethoxy]fluoren-9-one in 20 ml of ether and 50 ml of methanol is stirred and treated with approximately 0.085 mole of diazomethane which is co-distilled into the reaction mixture at 10°–28° C. with diethyl ether. The reaction mixture is stirred at room temperature for 24 hours and most of the volatile materials are removed in vacuo. The residue is treated with a dilute solution of sodium hydroxide and extracted several times with ether. The combined ether extracts are washed with water, dried over anhydrous sodium sulfate, treated with charcoal, filtered and the product converted to its hydrochloride salt by treatment with ethereal HCl. This salt is then dissolved in 200 ml of ethanol and treated with 3.8 g of Girards Reagent T to allow for the subsequent removal of any unreacted starting material. The resulting solution is refluxed for 3 hours, treated with 200 ml of a 5% sodium hydroxide solution and extracted with ether. The combined ether extracts are washed with water, dried and most of the volatile material removed. The resulting residue is dissolved in 40°–60° C. petroleum ether, filtered, placed on an alumina chromatographic column and eluted with 40°–60° C. petroleum ether. The initial eluate is collected, the volatiles removed and the 2,7-bis[2-(diethylamino)ethoxy]-9-methoxyphenanthrene so obtained is recrystallized from 40°–60° C. petroleum ether and again from pentane solution, m.p. 63°–65° C., $\lambda_{max}^{MeOH}$ 259, and $E_{1cm}^{1\%}$ 1590.

Following essentially the same procedure, but substituting for the 2,7-bis[2-(diethylamino)ethoxy]fluoren-9-one above, the appropriate molar equivalent quantities of 2,7-bis[2-(dibutylamino)ethoxy)ethoxy]fluoren-9-one, 2,7-bis[2-(diisopropylamino)ethoxy]fluoren-9-one, 2,7-bis[3-(dimethylamino)propoxy]fluoren-9-one and 2,7-bis[3-(dibutylamino)propoxy]fluoren-9-one, the following compounds are obtained: 2,7-bis[2-(dibutylamino)ethoxy]-9-methoxyphenanthrene, 2,7-bis[2-(diisopropyl-amino)ethoxy]-9-methoxyphenanthrene, 2,7-bis[3-(dimethylamino)propoxy]-9-methoxyphenanthrene and 2,7-bis[3-(dibutylamino)propoxy]-9-methoxyphenanthrene, respectively.

EXAMPLE III

2,7-Bis(3-piperidinopropoxy) fluoren-9-one dihydrochloride

A mixture of 63.6 g (0.30 mole) of 2,7-dihydroxyfluoren-9-one, 188 g (0.95 mole) of 1-(3-chloropropyl) piperidine hydrochloride, 132 g (2.0 mole) of 85% potassium hydroxide in 900 ml of toluene and 300 ml of water is refluxed with vigorous stirring for 20 hours. The layers are separated upon cooling and the organic layer is washed 3 times with water, once with a saturated solution of sodium chloride and dried over anhydrous magnesium sulfate. The mixture is filtered and the solvent removed in vacuo. The residue is taken up in isopropyl alcohol and acidified to Congo Red with ethereal hydrogen chloride. The solid which precipitates is filtered, recrystallized from a mixture of 3 parts isopropyl alcohol to 1 part methanol, and the 2,7-bis (3-piperidinopropoxy)fluoren-9-one dihydrochloride so prepared is dried at 100° C. for 24 hours under vacuum, m.p. 279.5°–80.5° C., $\lambda_{max}^{H2O}$ 270, and $E_{1cm}^{1\%}$ 1370.

EXAMPLE IV

9-Methoxy-2,7-bis(3-piperidinopropoxy) phenanthrene

A solution of 4.7 g (0.01 mole) of 2,7-bis(3-piperidinopropoxy)fluoren-9-one in methanol is stirred and treated with approximately 0.085 mole of diazomethane by co-distillation with ether into the reaction mixture at a temperature of −15° to −31° C. The reaction mixture is allowed to warm slowly to room temperature overnight. The volatile materials are removed on the steam bath in vacuo and the residue triturated with pentane to induce crystallization. The resulting solid is dissolved in a mixture of pentane and ether, washed several times with a dilute solution of sodium hydroxide, washed with water, dried over anhydrous sodium sulfate, treated with charcoal, filtered and most of the volatile solvents removed from the filtrate. The residue is recrystallized from pentane and again from a methanol-water mixture to yield the desired 9-methoxy-2,7-bis(3-piperidinopropoxy) phenanthrene: m.p. 118.5°–9.5° C., $\lambda_{max}^{MeOH}$ 259, and $E_{1cm}^{1\%}$ 1430.

Following essentially the same procedure, but substituting for the 2,7-bis(3-piperidinopropoxy)fluoren-9-one above, the appropriate molar equivalent quantities of 2,7-bis[2-(1-pyrrolydinyl)ethoxy]fluoren-9-one or 2,7-bis(4-morpholinobutoxy)fluoren-9-one results in the formation of 9-methoxy-2,7-bis[2-(1-pyrrolidinyl)ethoxy]phenanthrene and 9-methoxy-2,7-bis(4-morpholinobutoxy) phenanthrene, respectively.

EXAMPLE V

2,7-Bis[2-(dimethylamino)ethoxy]-9-phenanthrol

A solution of 8.1 g (0.023 mole) of 2,7-bis[2-(dimethylamino)ethoxy]fluoren-9-one in 50 ml of methanol and 25 ml of ether is stirred and treated with 0.5 gram of finely powdered sodium carbonate. To this mixture is added 75 g (0.06 mole) of ethyl N-methyl-N-nitrosocarbamate in 20 ml of methanol over a period of 2 hours. The temperature of this reaction mixture is kept below 30° C. for a period of 24 hours. The reaction mixture is then freed of most of the volatile materials in vacuo, dissolved in an aqueous solution of hydrochloric acid, and extracted several times with diethyl ether. The resulting aqueous solution is made strongly alkaline with an aqueous sodium hydroxide solution and extracted with ether. The remaining aqueous solution is neutralized to an approximate pH of 10 using a 10% hydrochloric acid solution and extracted with ether. Evaporation of the combined ether extracts in vacuo and recrystallization from a methanol-water mixture yields the desired 2,7-bis[2-(dimethylamino)

Preparation of the 9-loweralkoxy ethers is accomplished by further reacting a methanolic solution of 2,7-bis[2-(dimethylamino)ethoxy]-9-phenanthrol with a diazoloweralkane, such as diazoethane and diazopropane. The resulting 2,7-bis[2-(dimethylamino)ethoxy]-9-ethoxyphenanthrene and 2,7-bis[2-(dimethylamino)ethoxy]-9-propoxyphenanthrene so prepared can be isolated by removal of the volatile materials in vacuo and recrystalizing the residue from aqueous methanol.

EXAMPLE VI 3,8-Bis[2-(diethylamino)ethoxy]-6(5H)-phenanthridinone dihydrochloride Using the product prepared in accordance with Example I, 10 g (0.027 mole) of 2,7-bis[2-(diethylamino)ethoxy]fluoren-9-one dihydrochloride is dissolved in 75 ml of trifluoroacetic acid and chilled to a temperature of from 0°–5° C. Sodium azide, 3.5 g, is added in increments with stirring followed by 10 ml of sulfuric acid which is added in a dropwise fashion. Stirring and cooling is continued for an additional hour and the solution made alkaline with an excess of a 20% potassium hydroxide solution. The basic reaction mixture is extracted several times with methylene chloride, the extracts are combined, washed with water, dried over anhydrous sodium sulfate, filtered and the filtrate evaporated in vacuo. The residue is dissolved in ether and acidified with ethereal hydrogen chloride. Recrystallization of the residue from a mixture of methanol-butanone yielded 3,8-bis[2-(diethylamino)ethoxy]-6(5H)-phenanthridinone as the dihydrochloride salt having a m.p. of 250°–252° C., $\lambda_{max}^{EtOH}$ 230, and $E_{1cm}^{1\%}$ 885.

Following essentially the same procedure but substituting the appropriate molar equivalent amounts of 2,7-bis(2-piperidinoethoxy)fluoren-9-one dihydrochloride, 2,7-bis[3-(dimethylamino)propoxy]fluoren-9-one dihydrochloride and 2,7-bis[2-(diallylamino)ethoxy]fluoren-9-one dihydrochloride for the 2,7-bis[2-(diethylamino)ethoxy]fluoren-9-one dihydrochloride results in the formation of the following compounds, respectively: 3,8-bis(2-piperidinoethoxy)-6(5H)-phenanthridinone dihydrochloride, 3,8-bis[3-(dimethylamino)propoxy]-6(5H)-phenanthridinone dihydrochloride and 3,8-bis[2-(diallylamino)ethoxy]-6(5H)-phenanthridinone dihydrochloride.

EXAMPLE VII 3,8-Bis[2-(dimethylamino)ethoxy]-6H-dibenzo[b,d]pyran-6-one dihydrochloride A solution of 13.5 g (0.04 mole) of 2,7-bis(2-chloroethoxy)fluoren-9-one in 100 ml of concentrated sulfuric acid is slowly reacted with 12 ml of a 30% hydrogen peroxide solution at room temperature. The reaction which is strongly exothermic is controlled by cooling the stirred reaction mixture in an ice-water bath. The cooled reaction mixture is poured onto 500 ml of an ice-water mixture and the resulting 3,8-bis(2-chloroethoxy)-6H-dibenzo [b,d]pyran-6-one which separates is isolated.

A mixture of 4.6 g (0.013 mole) of 3,8-bis(2-chloroethoxy)-6H-dibenzo[b,d]pyran-6-one so obtained, 2 g of potassium iodide and 100 ml of a 40% aqueous dimethylamine solution contained in 50 ml of tetrahydrofuran is heated in a Parr pressure reactor with stirring at 120° C. for 16 hours. The reaction vessel is cooled and most of the volatile materials are removed in vacuo. The residue is treated with an aqueous sodium hydroxide solution and extracted with ether. The ether solution is washed twice with water, once with a saturated solution of sodium chloride, dried over anhydrous magnesium sulfate and treated with ethereal hydrogen chloride. The product which separates is then recrystalized from a methanol-anhydrous ether mixture to yield the desired 3,8-bis[2-(dimethylamino)ethoxy]-6H-dibenzo[b,d]pyran-6-one dihydrochloride.

EXAMPLE VIII

The following Example is illustrative of the antiviral activity for the compounds of the present invention. Thirty mice each weighing approximately 12 to 15 gms are divided into two groups, a control group containing 20 animals and a test group of 10 animals. All of the animals are challenged with a fatal dose ($28LD_{50}$) of encephalomyocarditis virus. The test group of animals are treated both prophylactically and therapeutically using a parenteral composition containing 3,8-bis[2-diethylamino)ethoxy]-6(5H)-phenanthridinone dihydrochloride as the active ingredient dissolved in an aqueous solution of 0.15% hydroxyethylcellulose. The composition contains the active ingredient in an amount such that each dosage contains 0.25 ml which is equivalent to a dose level of 50 mg per kg. The control group receives a subcutaneous placebo containing the same volume of vehicle without, of course, the active ingredient. Observations over a ten day period show a termination of all the control animals within a period of from 4 to 5 days, with the treated group of animals surviving for a statistically longer period of time.

EXAMPLE IX

Preparation of a tablet formulation

An illustrative preparation of 10,000 tablets, each containing 100 mg of 3,8-bis[2-(diethylamino)ethoxy]-6(5H)-phenanthridinone is prepared as follows:

|     |                                                             | Gm.  |
| --- | ----------------------------------------------------------- | ---- |
| (a) | 3,8-bis[2-(diethylamino)ethoxy]-6(5H)-phenanthridinone      | 1000 |
| (b) | Lactose                                                     | 1000 |
| (c) | Starch paste (10% w/v starch in water)                      | 100  |
| (d) | Starch                                                      | 32.5 |
| (e) | Calcium stearate                                            | 6.5  |

The active ingredient is uniformly mixed with the lactose and granulated by the addition of the starch paste. The granules which form are dried at 120° F. for 20 hours and forced through a No. 16 screen. The granules are lubricated by the addition of the starch and calcium stearate and compressed into tablets. Each tablet so prepared contains 100 mg of the active ingredient.

EXAMPLE X

Preparation of a capsule formulation

An illustrative composition for the preparation of 1000 two-piece hard gelatin capsules, each capsule containing 100 mg of 2,7-bis[2-(diethylamino)ethoxy]-9-methoxyphenanthrene is prepared as follows:

|                                                           | Gm. |
| --------------------------------------------------------- | --- |
| (a) 2,7-bis[2-(diethylamino)ethoxy]-9-methoxyphenanthrene | 100 |
| (b) Corn starch                                           | 150 |
| (c) Magnesium stearate                                    | 25  |
| (d) 1000 Hard gelatin capsules                            |     |

The finely powdered ingredients are mixed until uniformly dispersed and then filled into hard shelled gelatin capsules of the appropriate size.

In a similar fashion, soft gelatin capsules may be prepared in which the above composition can be granulated, slugged or directly compressed in a rotary die or plate mold in which the soft gelatin capsule is formed. Alternatively, the above excipients may be omitted and the active ingredient dispensed as a powder directly into the soft gelatin capsule.

EXAMPLE XI

Preparation of an oral syrup formulation

A 2% weight per volume syrup of 3,8-bis(4-piperidinobutoxy)-6(5H)-phenanthridinone dihydrochloride is prepared in accordance with the usual pharmaceutical techniques which has the following formula:

|  | Gm. |
|---|---|
| (a) Finely divided 3,8-bis(4-piperidinobutoxy-6(5H)-phenanthridinone dihydrochloride | 2.0 |
| (b) Sucrose | 33.3 |
| (c) Chloroform | 0.25 |
| (d) Sodium benzoate | 0.4 |
| (e) Methyl p-hydroxybenzoate | 0.02 |
| (f) Vanillin | 0.04 |
| (g) Glycerol | 1.5 |
| (h) Purified water to 100.0 ml | |

EXAMPLE XII

Preparation of ointment formulation

One thousand grams of an ointment for topical application containing 1.0% of 3,8-bis[2-(diethylamino)ethoxy]-6(5H)-phenanthridinone dihydrochloride is prepared from the following ingredients:

|  | Gm. |
|---|---|
| (a) 3,8-bis[2-(diethylamino)ethoxy]-6(5H)-phenanthridinone dihydrochloride | 10 |
| (b) Light liquid petrolatum | 250 |
| (c) Wool fat | 200 |
| (d) White petrolatum q.s. ad 1000 | |

The wool fat, white petrolatum and 200 gms of the light liquid petrolatum are liquified and held at 110° F. The active ingredient is mixed with the remaining liquid petrolatum and passed through a colloid mill. After passing through the mill, the mixture is stirred into the melt, and the melt is permitted to cool with continued stirring until congealed.

EXAMPLE XIII

Preparation of a parenteral emulsion formulation

An illustrative composition for an emulsion which is parenterally injectable is as follows:

| Each ml Contains | Ingredients | Amount |
|---|---|---|
| 50 mg | 3,8-bis[2-(diethylamino)ethoxy]-6(5H)-phenanthridinone | 1.000 g |
| 100 mg | Polyoxyethylene sorbitan monooleate | 2.000 g |
| 0.0064 | Sodium chloride | 0.128 g |

| Each ml Contains | Ingredients | Amount |
|---|---|---|
|  | Water for injection q.s. | 20.000 ml |

The parenteral composition is prepared by dissolving 0.64 g of sodium chloride in 100 ml of water suitable for injection. The polyoxyethylene sorbitan monooleate is mixed with the active ingredient, and an amount of the previously prepared aqueous sodium chloride solution added which is sufficient to bring the total volume to 20 ml. The resulting solution is shaken and autoclaved for 20 minutes at 110° C. at 15 p.s.i.g. steam pressure. The composition can be dispensed in a single ampule for use in multiple dosages or it can be dispensed in 10 or 20 individual ampules for use as a single dosage unit.

I claim:

1. A 3,8-bis-basic ether of 6H-dibenzo[b,d]pyran-6-one having the formula:

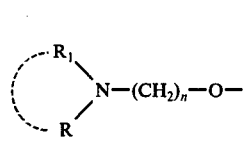

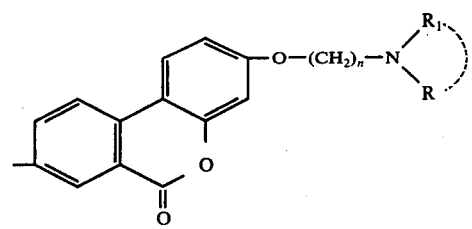

wherein $n$ is an integer of from 2 to 6; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group, and when R and $R_1$ are taken together with the nitrogen atom to which they are attached represent the pyrrolidinyl, piperidino or morpholino group; and the pharmaceutically acceptable acid addition salts thereof.

2. A compound according to claim 1 wherein R and $R_1$ are loweralkyl having from 1 to 6 carbon atoms.

3. The compound 3,8-bis[2-(dimethylamino)ethoxy]-6H-dibenzo[b,d]pyran-6-one and its pharmaceutically acceptable acid addition salts thereof.

4. A method of preventing viral infections which comprises the daily prophylactic administration of from 0.1 milligrams to 500 milligrams per kilogram of body weight of a compound of claim 1 to a host susceptible to infection by pathogenic viral agents.

5. A method of treating viral infections which comprises administering from 0.1 milligrams to 500 milligrams per kilogram of body weight per day of a compound of claim 1 to an infected host.

6. An antiviral composition in dosage unit form comprising from 2 milligrams to 3 grams of a compound of claim 1 and a pharmaceutical carrier.

7. An oral dosage unit of antiviral composition comprising from 2 milligrams to 3 grams of a compound of claim 1 and a pharmaceutical carrier.

* * * * *

UNITED STATES PATENT OFFICE
CERTIFICATE OF CORRECTION

Patent No. 4,059,702  Dated November 22, 1977

Inventor(s) Donald R. Meyer

It is certified that error appears in the above-identified patent and that said Letters Patent are hereby corrected as shown below:

Cover Page, Item [45] "Nov. 22, 1976" read -- Nov. 22, 1977 --.
Column 3, line 45, "-CH$_+$" should read -- -CH= --.

Column 10, lines 52 and 53, "fluorenous" should read -- fluorenone --.

Column 13, last structure

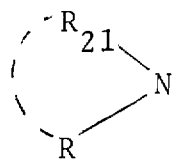   should read   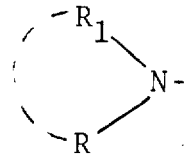

Column 19, lines 15 and 16, "2,7-BIS 2-(diethylamino)ethoxy]-9-methoxyphenanthrene" should read -- 2,7-Bis[2-(diethylamino)ethoxy]-9-methoxyphenanthrene --. Column 19, line 49, "(dibutylamino)ethoxy)ethoxy]" should read -- (dibutylamino)ethoxy] --. Column 20, line 64, "2,7-bis]2-(dimethylamino)" should read -- 2,7-bis]2-(dimethylamino)ethoxy]-9-phenanthrol. -

Signed and Sealed this

Second Day of May 1978

[SEAL]

Attest:

RUTH C. MASON
Attesting Officer

LUTRELLE F. PARKER
Acting Commissioner of Patents and Trademarks